US008891734B2

(12) United States Patent
Lalena et al.

(10) Patent No.: US 8,891,734 B2
(45) Date of Patent: Nov. 18, 2014

(54) PORTABLE DIGITAL RADIOGRAPHY DETECTOR LOSS PREVENTION

(75) Inventors: Michael C. Lalena, Webster, NY (US); Peter A. Newman, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 346 days.

(21) Appl. No.: 13/429,728

(22) Filed: Mar. 26, 2012

(65) Prior Publication Data

US 2013/0094628 A1 Apr. 18, 2013

Related U.S. Application Data

(60) Provisional application No. 61/546,096, filed on Oct. 12, 2011.

(51) Int. Cl.
*H05G 1/54* (2006.01)
*A61B 6/00* (2006.01)

(52) U.S. Cl.
CPC .............. *A61B 6/4283* (2013.01); *A61B 6/547* (2013.01); *A61B 6/4405* (2013.01); *A61B 6/4494* (2013.01)
USPC .......................................... 378/116; 378/198

(58) Field of Classification Search
CPC .... A61B 6/547; A61B 6/4494; A61B 6/4405; A61B 6/4233
USPC .................... 378/98, 98.8, 114–116, 198; 250/370.08, 370.09
See application file for complete search history.

(56) References Cited

U.S. PATENT DOCUMENTS

| 5,844,961 | A | 12/1998 | McEvoy |
| 7,611,282 | B2 | 11/2009 | Koren |
| 2005/0063512 | A1 | 3/2005 | Maschke |
| 2006/0188071 | A1 | 8/2006 | Spahn |
| 2007/0153980 | A1* | 7/2007 | Butzine et al. ................. 378/198 |
| 2009/0130983 | A1 | 5/2009 | Venturina et al. |
| 2009/0278047 | A1 | 11/2009 | Nishino et al. |
| 2011/0274244 | A1* | 11/2011 | Jabri et al. ...................... 378/62 |

FOREIGN PATENT DOCUMENTS

| WO | WO 2007/078684 | 7/2007 |
| WO | WO 2007/139638 | 12/2007 |

OTHER PUBLICATIONS

International Search Report, International Application No. PCT/US2012/052954, Jan. 30, 2013, 2 pages.

* cited by examiner

*Primary Examiner* — Courtney Thomas

(57) ABSTRACT

A method for managing a portable x-ray detector for an x-ray imaging apparatus registers at least one portable detector with a processor that is associated with the x-ray imaging apparatus. A generated signal is indicative of the location of the registered portable x-ray detector relative to the x-ray imaging apparatus. An alert indication is provided when the generated signal indicates separation of the registered portable x-ray detector from the x-ray imaging apparatus beyond a predetermined distance.

20 Claims, 16 Drawing Sheets

PORTABLE DIGITAL RADIOGRAPHY DETECTOR LOSS PREVENTION

CROSS REFERENCE TO RELATED APPLICATIONS

Reference is made to, and priority is claimed from, U.S. Ser. No. 61/546,096, filed as a provisional patent application on Oct. 12, 2011, entitled "PORTABLE DIGITAL RADIOGRAPHY DETECTOR LOSS PREVENTION", in the names of Michael Lalena and Peter Newman and which is commonly assigned.

FIELD OF THE INVENTION

The invention relates generally to the field of medical imaging, and in particular to a radiographic imaging apparatus for capturing analog and digital medical images.

BACKGROUND

Stationary radiographic imaging equipment are employed in medical facilities (e.g., in a radiological department) to capture (e.g., digital) medical x-ray images on x-ray detector. Mobile carts are employed in medical facilities to move medical equipment between locations. One type of mobile cart includes an x-ray source used to capture (e.g., digital) x-ray images on x-ray detector. Medical x-ray images can be captured using various techniques such as computed radiography (CR) and digital radiography (DR).

Refer also to U.S. Pat. No. 7,611,282 (Koren) and WO 2007/139638 (Jadrich), and WO 2007/078684 (Dhurjaty), and U.S. Pat. No. 5,844,961 (McEvoy).

Mobile x-ray apparatus are of particular value in intensive care unit (ICU) and other environments where timely acquisition of a radiographic image is important. Because portable carts can be wheeled around the ICU or other area and brought directly to the patient's bedside, a portable x-ray imaging apparatus allows an attending physician or clinician to have recent information on the condition of a patient and helps to reduce the risks entailed in moving patients to stationary equipment in the radiological facility.

However, there is a need for improvements in detector loss prevention and in particular to portable DR detector loss prevention when used with medical radiographic portable and/or in-room medical imaging systems.

SUMMARY OF THE INVENTION

An aspect of this application is to advance the art of medical radiography.

Another aspect of this application to address in whole or in part, at least the foregoing and other deficiencies in the related art.

It is another aspect of this application to provide in whole or in part, at least the advantages described herein.

An aspect of this application to is to address the need for detector loss prevention.

In accordance with one embodiment, the present invention can provide a method for managing a portable x-ray detector for an x-ray imaging apparatus, the method comprising: registering at least one portable detector with a processor that is associated with the x-ray imaging apparatus; generating a signal that is indicative of the location of the registered portable x-ray detector relative to the x-ray imaging apparatus; and providing an alert indication when the generated signal indicates separation of the registered portable x-ray detector from the x-ray imaging apparatus beyond a predetermined distance.

In accordance with an alternate embodiment, the present invention can provide a method for reducing portable detector loss for a portable x-ray imaging apparatus, that can include associating an operator with the portable x-ray imaging apparatus registering at least one portable detector portable x-ray imaging apparatus; identifying a first patient and at least one x-ray image to be taken for the first patient; and providing an alert indication at the portable x-ray imaging apparatus when the at least one detector is greater than a prescribed distance from the portable x-ray imaging apparatus.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DESCRIPTION OF EXEMPLARY EMBODIMENTS

Figure 1:
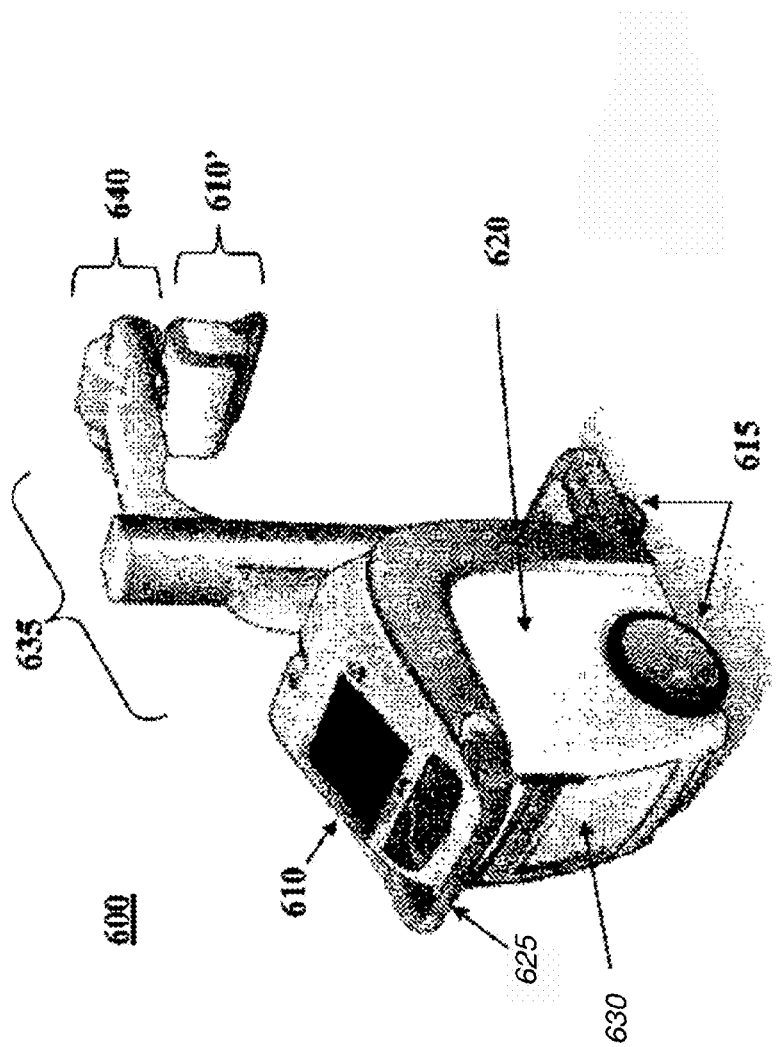
FIG. 1 is a diagram that shows a perspective view of a mobile radiography unit according to one embodiment of the application.

The following is a description of exemplary embodiments of the invention, reference being made to the drawings in which the same reference numerals identify the same elements of structure in each of the several figures. Where they are used, the terms "first", "second", and so on, do not necessarily denote any ordinal or priority relation, but may be used for more clearly distinguishing one element or time interval from another.

FIG. 1 is a diagram that shows a perspective view of a mobile radiography unit capable of prior images display according to an embodiment of the application. The exemplary mobile x-ray or radiographic apparatus of FIG. 1 can be employed for computed radiography (CR) and/or digital radiography (DR). As shown in FIG. 1, a mobile radiography apparatus 600 can include a moveable transport frame 620 that includes a first display 610 and an optional second display 610' for display relevant information such as obtained images and related data. Either or both displays 610 and 610' can be touch screen displays. As shown in FIG. 1, the second display 610' can be pivotably mounted at the x-ray source 640 to be viewable/touchable from a 360 degree area around the tube head.

The displays 610, 610' can implement or control functions such as generating, storing, transmitting, modifying, and printing of an obtained image or images and can optionally include an integral or separate control panel (not shown) to assist in implementing functions such as generating, storing, transmitting, modifying, and printing for an obtained image.

For mobility, the mobile radiographic apparatus 600 has one or more wheels 615 and one or more handle grips 625, typically provided at waist-, arm-, or hand-level, that help to guide the mobile radiography apparatus 600 to its intended location. A self-contained battery pack (e.g., rechargeable) typically provides source power, which can reduce or eliminate the need for operation near a power outlet. Further, the self-contained battery pack can provide for motorized transport.

For storage, the mobile radiography apparatus 600 can include an area/holder for holding/storing one or more digital detectors or computed radiography cassettes. The area/holder can be storage area 630 (e.g., disposed on the frame 620) configured to removably retain at least one digital radiography (DR) detector. The storage area 630 can be configured to hold one or more detectors and can also be configured to hold one size or multiple sizes of detectors.

Mounted to frame 620 is a support column 635 that supports an x-ray source 640, also called an x-ray tube, tube head, or generator that can be mounted to the support column 635. In the embodiment shown in FIG. 1, the support column 635 can include a second section that extends outward a fixed/variable distance from a first section where the second section is configured to ride vertically up and down the first section to the desired height for obtaining the image. In another embodiment, the tube head or x-ray source 640 can be rotatably coupled to the support column 635. In another exemplary embodiment, an articulated member of the support column 635 that bends at a joint mechanism can allow movement of the x-ray source 640 over a range of vertical and horizontal positions. Height settings for the x-ray source 640 can range from low height for imaging feet and lower extremities to shoulder height and above for imaging the upper body portions of patients in various positions.

Figure 2:
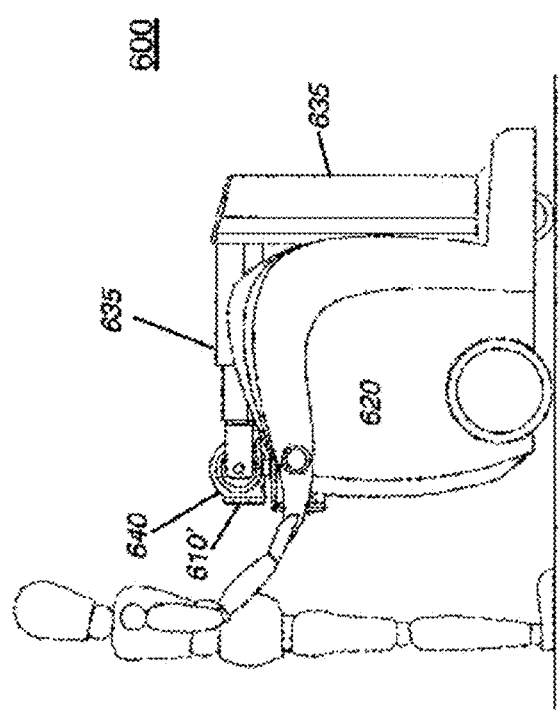
FIG. 2 is a diagram that shows a perspective view of a mobile radiography unit of FIG. 1 positioned for travel.

As shown in FIG. 2, for ease during transport of the mobile radiography apparatus 600, the support member 635 and x-ray source 640 can be arranged close to frame 620. As shown in FIG. 2, the second display 610' can be moved to a viewable position (e.g., operable) during transport of the mobile radiography apparatus 600. In one embodiment, the first display 610 can be disabled during transport. When the mobile radiography apparatus 600 is to be used, the support member 635 and x-ray source 640 can be extended from the frame 620 for proper positioning (e.g., by the operator, a user, or x-ray technician) and the second display 610' moved to viewable position as shown in FIG. 1.

According to exemplary embodiments of the application, the first display 610 and the second display 610' can provide information such as but not limited to: (i) general information such as date, time, environment conditions, and the like; (ii) unit information such as model serial number, operating instructions, warning information, and the like; (iii) patient data, such as patient name, room number, age, blood type, and the like; (iv) indicators such as but not limited to cart power/battery indicators, detector status (e.g., on/off), wireless signal strength/connectivity, grid alignment aides, cart diagnostics and/or (v) imaging/procedure information, such as the exam type, exposure information, and the like.

According to embodiments of the application, the first display 610 and the second display 610' can provide capabilities/functionality to the mobile radiography apparatus 600 such as but not limited to: (i) view and/or change x-ray exposure parameters, tube/generator/technique settings; (ii) view and/or change image information, such as a list of views (e.g., body part & projection) to perform for the patient, relevant information about those views, the ability to select a view to perform, and an x-ray image of an acquired view; (iii) display and/or change patient information, such as: Patient Name, Room number, Patient ID, date of birth (e.g., to confirm that the correct patient); (iv) display and/or change a Patient Worklist, such as a list of exams to perform and allow the user to select an exam (In one embodiment, such a patient worklist can be automatically updated (e.g., synchronized to a master/hospital/doctor worklist) using a wired or wireless network/connection. In one embodiment, the mobile radiography apparatus 600 can highlight/indicate new exams (e.g., on the second display 610') upon receipt of the scheduled examination); (v) display generator/source current values and controls to change those values, such as: kVp, mA, mAs, Time, ECF, focal spot, collimator, filter, AEC, grid; (vi) display detector selection and allow the technician to select/activate a different detector; (vii) display recently acquired images and allow editing of those images, exemplary acquired (e.g., recently) or previous images can be displayed full size, partial size or with corresponding image information; (viii) display previously acquired images (e.g., related prior images of a patient) and allow editing of those images; or (ix) display a video of what is in front of the mobile radiography apparatus 600 during transport, e.g., using a video camera located on the other side (e.g., front side of a mobile x-ray imaging apparatus 600).

Conventional solutions for image storage and retrieval and for association of multiple images obtained for the same patient employ the PACS (Picture Archiving and Communication System) and various conventional database tools. Thus, as described herein, the PACS is an image store accessible to a radiographic imaging system or an agent thereof to retrieve images therefrom. In one embodiment, the PACS can implement the Digital Imaging and Communications in Medicine (DICOM) data interchange standard.

Figure 3:
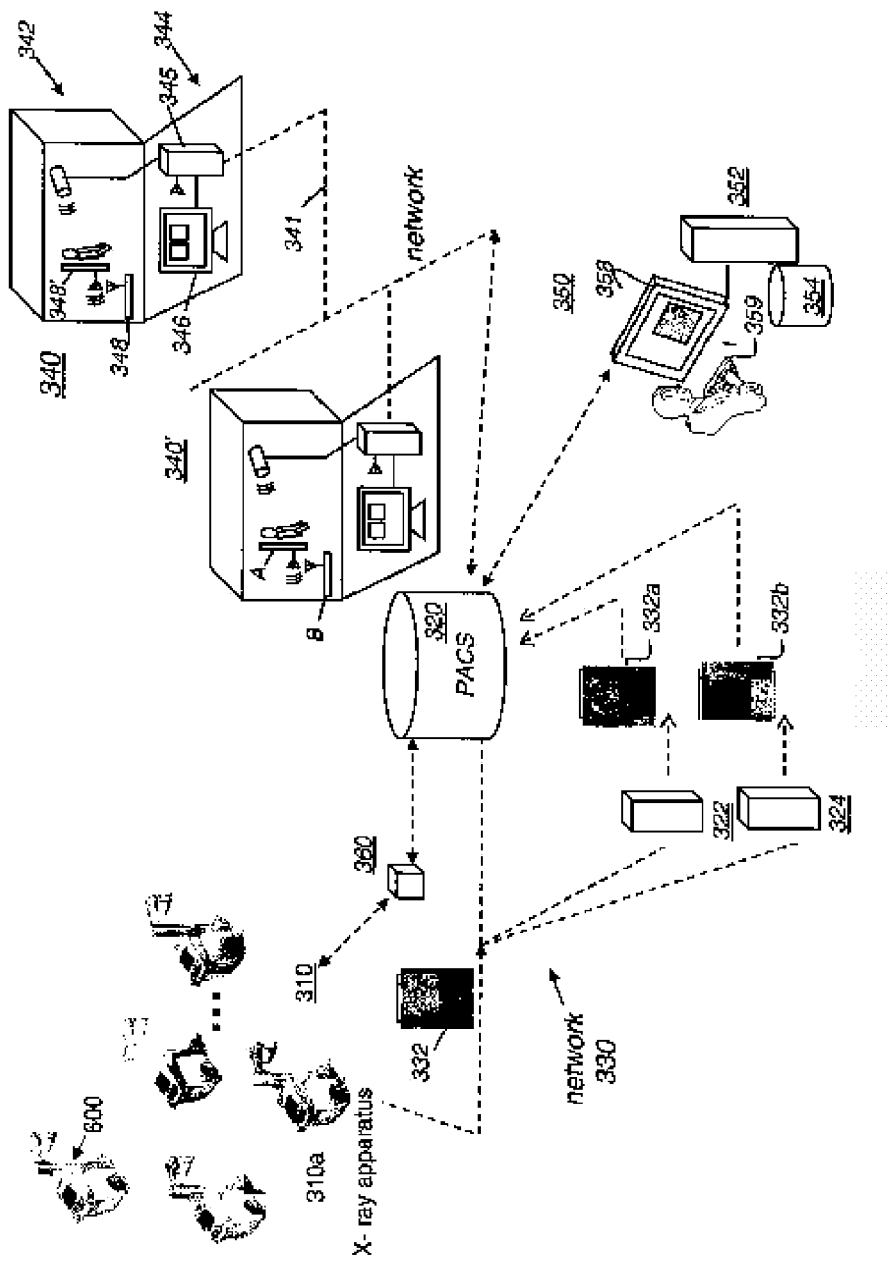
FIG. 3 is a schematic block diagram that shows a system for medical image procurement and management.

The schematic diagram of FIG. 3 shows an exemplary relationship of acquisition digital radiographic imaging apparatus (e.g., mobile DR imaging apparatus 310, x-ray imaging room 340), reviewing radiographic imaging apparatus (e.g., workstation 350) and/or storage radiographic imaging apparatus (e.g., PACS 320). As noted previously, a primary image 332 can be obtained from an image capture by a mobile DR imaging apparatus 310a. Primary image 332 can be directly provided for storage in the PACS 320 either as raw or pre-processed image data. Alternatively, the primary image 332 can be stored at the mobile DR imaging apparatus 310a and provided later to the PACS 320.

As shown in FIG. 3, an image management system 350 coupled to the system can include a logic processor 352, a memory 354, and an operator console that can include a display 358 and an operator entry device 359, such as a keyboard, mouse, touch screen, or other device for entry of operator commands. Commands at image management system 350 provide an additional capability for retrieval, review and/or management of the images stored in the system (e.g., PACS).

Still referring to FIG. 3, also connected to PACS 310 can be one or more X-ray imaging rooms 340 that can include an imaging room 342 (e.g., a shielded area in which a patient is imaged and containing an x-ray source), and a control room 344 that can include a display 346 and controller 345 for communicating with DR detectors 348 over a wireless interface and containing control logic for supporting and executing imaging operations with a selected DR detector 348. In the embodiment shown, display 346 can be a touch screen display, enabling the operator or technologist to easily control the X-ray imaging room 340 and select among DR detectors 348 as an active DR detector 358' for obtaining the image using a graphical user interface (GUI). Imaging rooms 340 can be connected to the PACS 320 using a network 341 (e.g., wired, wireless, proprietary, public). Further, a communication network 330 can interconnect the PACS 320 with the mobile DR imaging apparatus 310 (directly or via an additional image acquisition server 360), the additional image acquisition server 360, the x-ray imaging room 340 and/or the image management system 350. The communication network 330 may be wired, wireless, proprietary, or public and comprised of many interconnected computer systems and communication links. Communication links may be hardwire links, optical links, satellite or other wireless communication links, wave propagation links, or any other mechanisms for communication of information.

Primary image 332 can be provided to one or more logic processors 322, 324 that each can perform some type of image processing and analysis operation before the primary images 332a and 332b can be stored in the PACS 320 along with acquired primary image 332. As shown in FIG. 3 the primary image 332 can be pre-processed and suitable for storage/archival as it is provided from mobile DR imaging apparatus 310a. It should be noted that, in an alternate embodiment, primary image 332 may be provided as raw data, requiring some amount of processing prior to storage in PACS 320. Logic processors 322 and 324 can generate additional processed secondary images 332a and 332b from raw data or from pre-processed primary image 332, as shown in FIG. 3. In one embodiment, the additional processed secondary images 332a and 332b can be companion images.

In one embodiment, the mobile radiography apparatus 600 (FIG. 1) can be used as one of the plurality of portable DR imaging apparatus 310 (FIG. 3).

The portability of digital DR detectors has significant advantages over the x-ray film cassettes that they have replaced, but presents new problems for administration of radiography equipment. One difficulty with the configuration of mobile radiography apparatus 600 in FIGS. 1-3 relates to potential loss of the DR detector. Detector loss can happen in any of a number of different ways. Loss of the detector can occur as a result of patient travel, as the patient is transported to and from the radiography room. For example, it may be determined that the patient is too sick to move to the exam table. Instead, the exam is performed in the x-ray room, but with the patient in bed. The X-Ray technician slides detector under patient and performs the exam. The orderly then transports the patient back to the hospital room with the detector still positioned under the patient. The X-Ray technician may not readily be able to determine the location of the patient's room or whom to contact to obtain the misplaced DR detector. In a similar way, detector loss can occur when the technician wheels a portable radiography system into the patient's room, obtains the image, then inadvertently leaves the detector behind. Detector loss can also occur through theft or unauthorized removal for use at another site or facility.

Opportunity for loss of the DR detector can be mitigated by properly associating or registering a particular DR detector 348 with its corresponding mobile radiography apparatus 600, or more generally with a particular radiography system 30, and in maintaining that association in the work environment, while sensing that the distance between the DR detector 348 and its associated radiography system 30 is within predetermined or prescribed limits. With mobile radiography apparatus 600, the DR detector 348 travels with the portable system, but is removed from its storage area in the system and positioned behind the patient for imaging. Even with some visible marking scheme, it is possible for the technician to inadvertently separate the DR detector 348 from its associated x-ray system, whether the system is portable or stationary, or to confuse one DR detector for another. Because the detector is designed to travel from one bedside to another, it is possible for the DR detector to be misplaced, inadvertently left in position behind the patient in the hospital bed, restored to a storage position within the wrong imaging system, or moved away from the imaging system for one reason or another. This problem becomes particularly acute with the development of wireless data transmission, since cable connection is no longer needed for transferring image data from the DR detector to the system processor. Embodiments of the present invention address the need to more positively associate a given DR detector 348 with its target radiography apparatus and to alert the operator or other hospital personnel when it appears that a DR detector 348 may have been misplaced, lost, taken from its intended location, or left behind the patient. The methods described sense when the registered DR detector 348 is, in some way, separated from its corresponding system 30 beyond a prescribed distance, such as beyond about 20 feet, beyond about 40 feet, or beyond some other predetermined distance. This relative separation distance may be programmed and changeable, which would be appropriate for a mobile radiography apparatus, or may be fixed, such as triggered by crossing a threshold, such as the entrance-way to a designated radiography room or area. Thus, when a signal is generated that indicates that this predetermined distance is exceeded, the signal may indicate an actual distance measurement, such as in meters or feet, a distance inferred from relative signal strength or from loss of signal, or a distance indicated by detection of the device near or crossing a threshold, for example.

Figure 4:
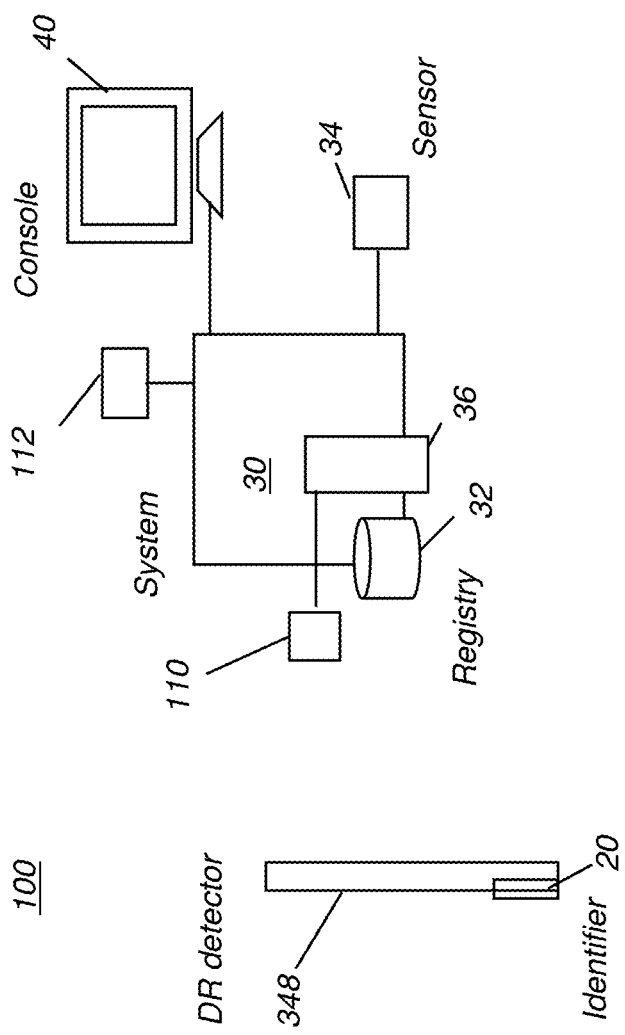
FIG. 4 is a schematic block diagram that shows components of a tracking system for a portable DR detector according to an embodiment of the present invention.

The schematic block diagram of FIG. 4 shows components of a tracking system 100 for management of DR detector 348 status and location. An identifier 20, described in more detail subsequently, provides a unique identifying mechanism for a particular detector 348. Identifier 20 is used to link DR detector 348 to one or more x-ray systems 30, which may be one or more stationary x-ray installations or one or more mobile radiography systems 600 that travel throughout a site. System 30 has an associated processor 36, such as a computer or dedicated logic processor, that maintains a registry 32 of one or more associated DR detectors 348. Registry 32 is a memory for storage of linkage information and other status information about one or more DR detectors 348 and associates the detectors 348 with system 30. The act of registering DR detector 348 to system 30 in registry 32 may be performed by operator entry at a control console 40 or by an automatic or semi-automatic method using an optional registration sensor 34. According to one embodiment of the present invention, registration sensor 34 is a switch or proximity sensor on the mobile radiography apparatus that provides a signal indicative of the presence or absence of the detector 348 from its transport position. According to an alternate embodiment of the present invention, registration sensor 34 and identifier 20 are both near field communications (NFC) RF device or other two-way communications device that communicates with each other when in close proximity.

Registration is not solely for loss prevention, but typically has other purposes, such as to validate data only from appropriate DR detectors 348, to help prevent confusion so that only data from a registered DR detector 348 is transferred to system 30. According to an embodiment of the present invention, registration identifies a particular DR detector 348 to an x-ray imaging system 30, so that images from that detector 348 may be acquired at the imaging system 30. System 30 has multiple DR detectors 348 registered, according to one embodiment, but is set up to communicate only with one designated DR detector at a time. Thus, a library of available DR detectors 348 can be maintained at system 30 so that one or another detector can be designated for a particular imaging situation. System 30 can maintain calibration files or other information for a number of DR detectors 348 in an active listing, from which the designated DR detector for a particular exam can be selected. De-registration can be used to make a particular DR detector 348 inactive or inaccessible from a particular system. However, the system 30 may maintain calibration and other data for a de-registered DR detector 348, so that the same device can be registered back to the system in the future.

The use of registration in this manner can be particularly useful in a wireless environment, so that data associated with a particular patient is properly acknowledged, identified, and transferred from DR detector 348. Tracking system 100 includes one or more indicators 110 that alert personnel to a discrepancy in detector tracking detected by the system. Alert indicator 110 may be a discrete device, such as an audible alarm, a light emitter, or other element that generates an audible or visible signal, or a message or symbol that displays on a control monitor, for example. It should be noted that tracking system 100 may be provided on mobile radiography apparatus 600, using a logic processor and other components provided and built into transport frame 620, or may be resident in processor 36 at a location that is associated with a stationary x-ray system 30 site. Alternately, a centralized server (FIG. 3) can store information for all portable DR detectors 348 at a site, and serve as a central repository and hub for detector location data. The alert may be provided at the target x-ray system 30 or at the DR detector 348 itself, such as with a beeping sound generated at the DR detector 348. A visual indicator at DR detector 348 may also be used, separately or in conjunction with an audible indicator. In an alternate embodiment, the alert indication is provided at both the system 50 and the detector 348. In another alternate embodiment, a display device that is part of detector 348 or coupled to detector 348 can provide text or symbolic information that indicates removal of the detector from its proper location. According to an alternate embodiment of the present invention, a text message is provided on the display device that indicates the correct location for return of the DR detector 348.

Figure 5:
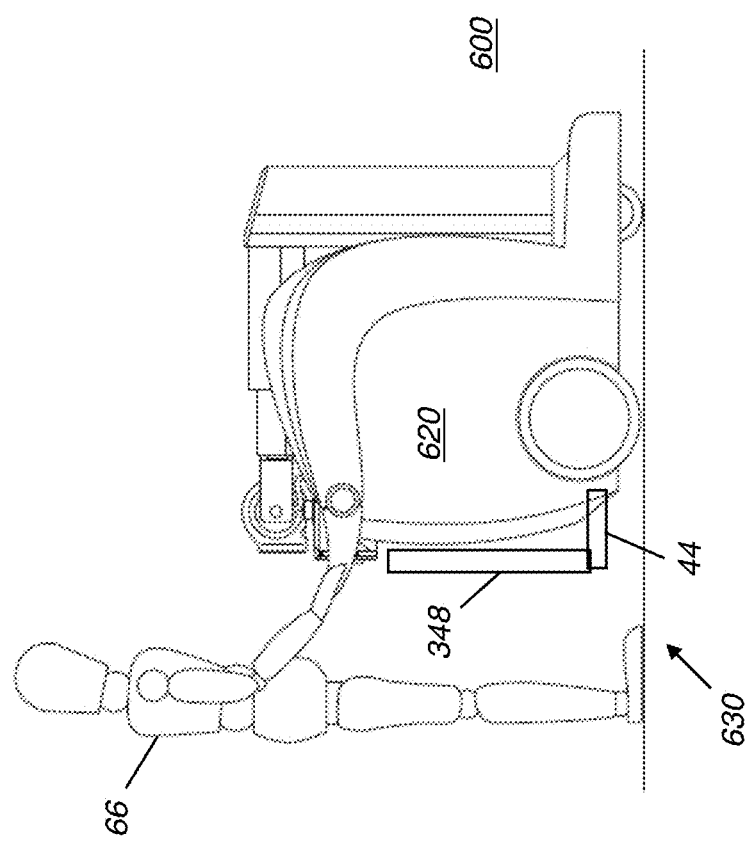
FIG. 5 is a side view diagram that shows a portable digital radiography apparatus with a DR detector.

The schematic block diagram of FIG. 5 shows a registered DR detector 348 that is used for a particular mobile radiography apparatus 600. A sensor 44 detects DR detector 348 seated properly in place in a holder within storage area 630 on the side of mobile apparatus 600. Sensor 44 can be, for example, a switch, such as a mechanical or proximity switch, a radio-frequency identifier (RFID) device, or a sensor that senses and obtains information from a light emitting diode (LED) or other light source on the detector itself. Registry 32 (not shown in FIG. 5) is maintained at a processor associated with mobile apparatus 600, as described earlier with reference to FIG. 4.

Figure 6:
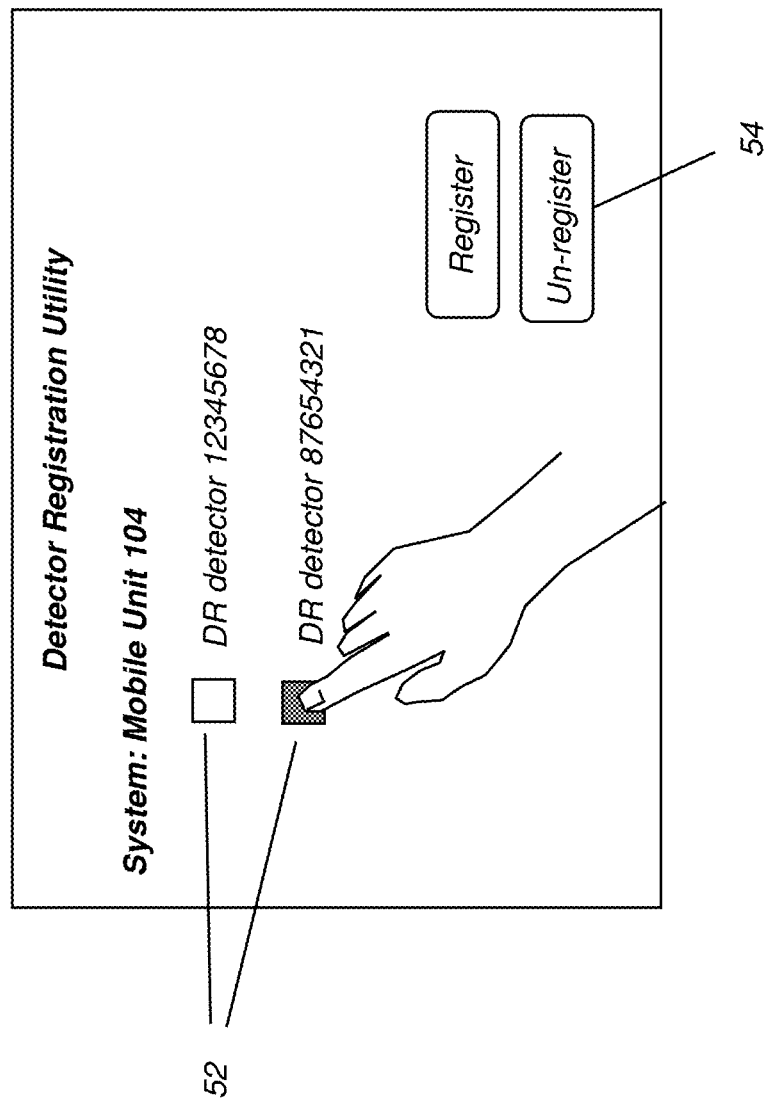
FIG. 6 is a plan view of a user interface screen for registering a portable DR detector.

The plan view of FIG. 6 shows an example registration screen 50 at an operator console, that may be located on mobile radiography apparatus 600 or at a stationary x-ray apparatus, as was described with reference to FIG. 4. One or more selection controls 52 enable operator selection for registration of one or more DR detectors 348 that can be associated with the system. A touch screen interface is shown in this example. The operator selects one or more DR detectors 348 according to a code or other identifying data associated with identifier 20 (FIG. 4). Instruction controls 54 enable registration or de-registration of each selected DR detector 348.

Once DR detector 348 is registered with system 30, a number of mechanisms can be used to track location and status of DR detector 348. FIGS. 7-11 show examples of some types of detection methods using tracking system 100 based on the location of registered DR detector 348 relative to stationary threshold locations at a particular site.

Figure 7:
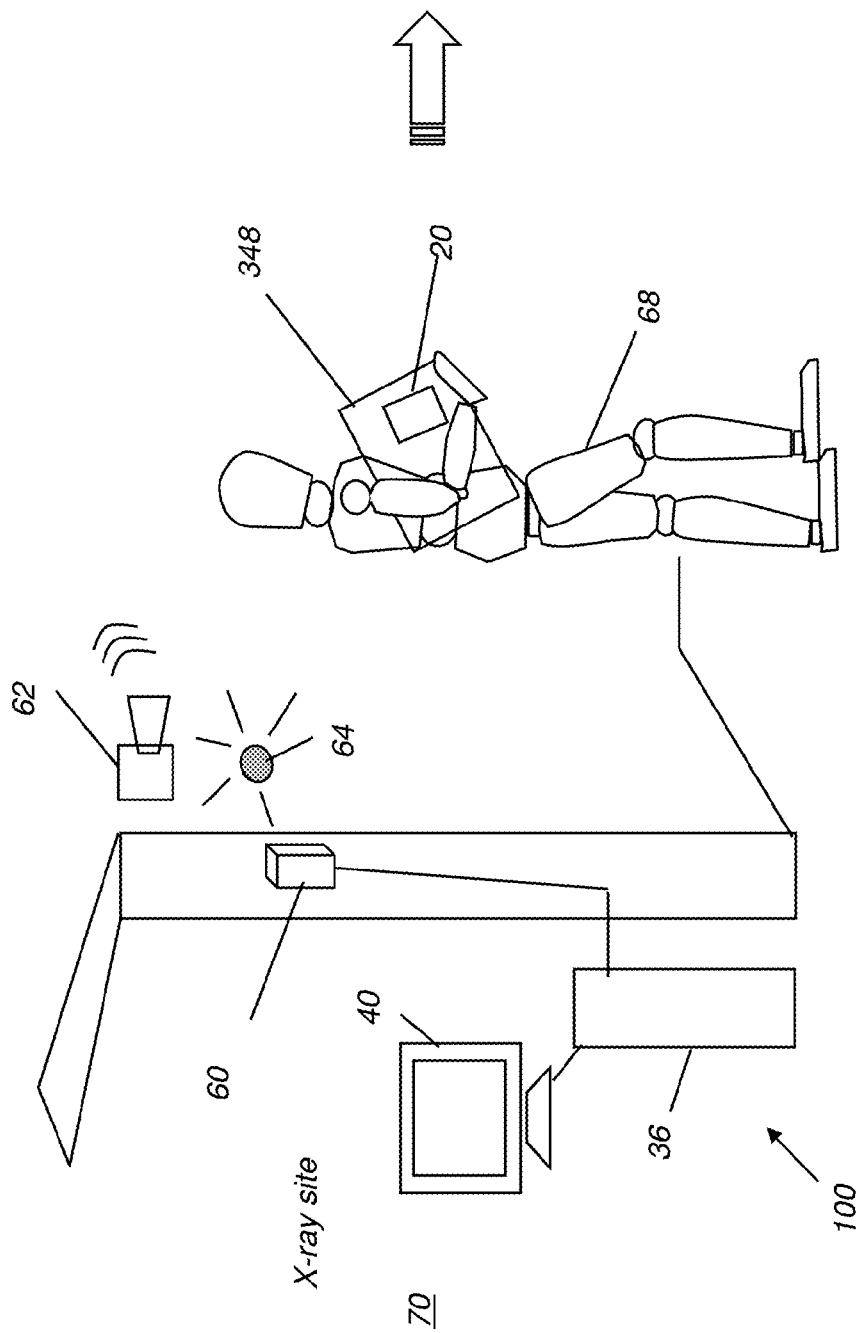
FIG. 7 is a schematic block diagram showing detection of a registered DR detector in transit relative to a stationary x-ray facility.

The schematic block diagram of FIG. 7 shows detection of registered DR detector 348 relative to a stationary x-ray system 30, such as provided at a radiography facility or other x-ray site 70. A sensor 60 located at an entrance to site 70 or other suitable location detects threshold events. When registered DR detector 348 is in transit and passes a threshold location, this indicates the likelihood of loss or misplacement, based on the relative distance between the detector 348 and its associated system 30 in the x-ray room, site 70. Sensor 60 sends a signal to processor 36 indicating transit of this DR detector 348 outside of its normal, expected or allowed distance range. Based on predetermined permissions set up for site 70, processor 36 may or may not activate an alarm 62, such as an audible alarm mounted near the entrance as shown in FIG. 7. Alternately, an indicator 64 is energized to signal detection of registered DR detector 348 in transit past sensor 60. In an alternate embodiment, this event is signaled at control console 40, with an audible signal, a text message, or other indication. In FIG. 7, a technician 68 or other person is exiting site 70 with registered DR detector 348. Both alarm 62 and indicator 64 are energized by tracking system 100 to signal this event, so that appropriate action can be taken. If movement is permitted, for example, it may be necessary to de-register DR detector 348 in order to allow it to be removed from site 70. As noted previously, de-registration may not delete information about a particular DR detector 348; de-registration may simply remove the particular DR detector 348 from an active status with respect to system 30. Alternately, a separate type of indicator (not shown), worn or carried by technician 68, may provide a signal that allows override of an alarm indication, such as indicating that a supervisor authorized to remove detector 348 beyond the threshold distance is responsible. It should be further noted that a combination of sensors can be used, as well as multiple sensors at different locations within or outside of a radiography room or other facility.

Processor 36 in FIG. 7 could be any of a number of different types of logic processing device that is in communication with sensor(s) 60 and alarm(s) 62. For example, processor 36 may be a computer or other processor that is provided as part of a mobile DR imaging apparatus. Processor 36 could alternately be a processor that is shared by a number of different DR imaging systems, mobile or stationary. In an alternate embodiment, processor 36 is a dedicated logic processor, such as a microcomputer device, that is installed specifically for tracking components such as the DR detector. Processor 36 may also be part of a logic control system for access control to the radiology facility.

Figure 8:
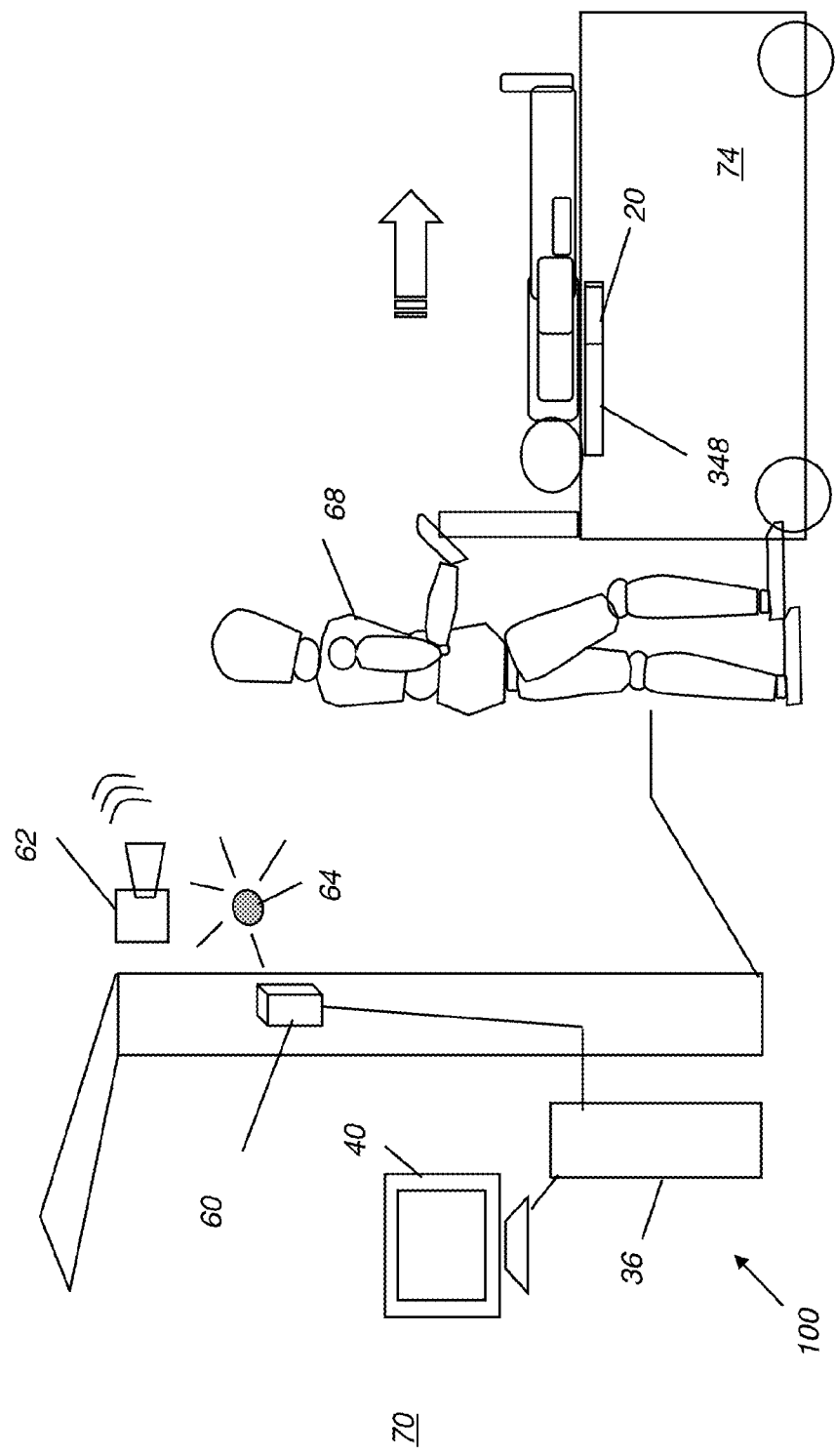
FIG. 8 is a schematic block diagram showing detection of a registered DR detector in transit relative to a stationary x-ray facility, with a patient transported out from the facility.
Figure 9:
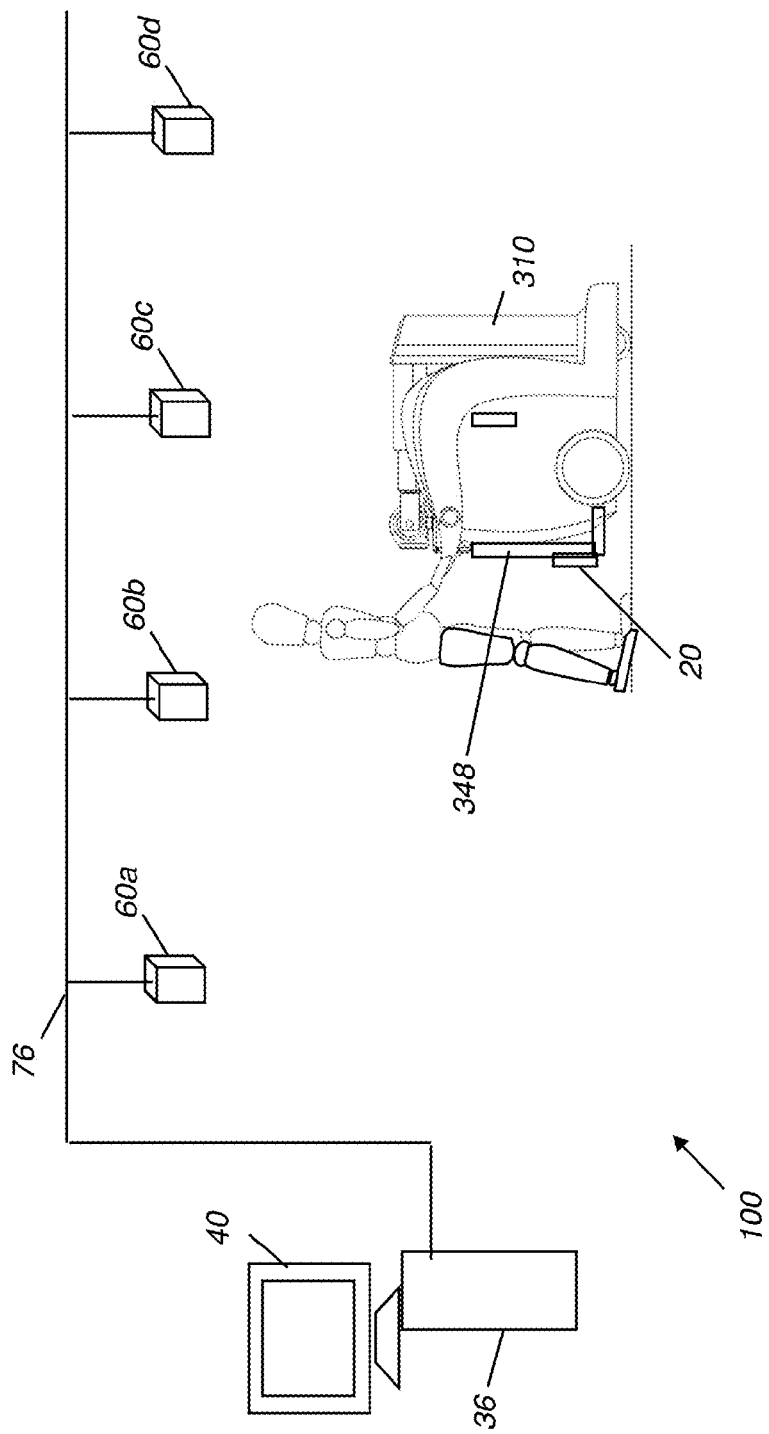
FIG. 9 is a schematic block diagram that shows a network of sensors for sensing the position of a portable DR detector in transit according to an embodiment of the present invention.
Figure 10:
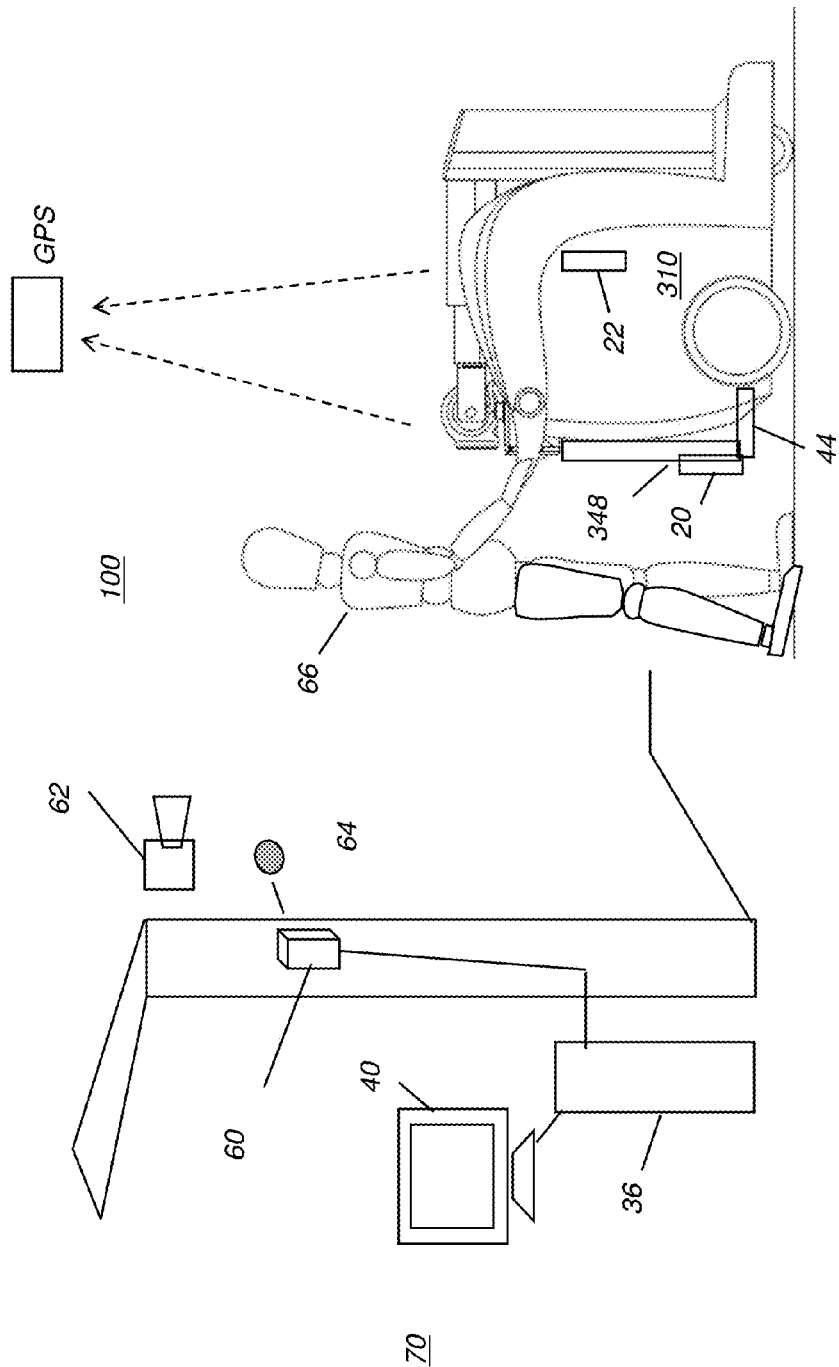
FIG. 10 is a schematic block diagram that shows the use of a remote sensing system for DR detector position sensing.

In FIG. 8, technician 68 is wheeling a patient bed 74 out from x-ray site 70, unaware that DR detector 348 is still positioned underneath the patient. This causes one or both of alarm 62 and indicator 64 to be energized to warn of detector removal. Management personnel must then de-register DR detector 348 in order to allow its removal without activating the warning devices. Alternately, a supervisory or other override can be provided to allow DR detector 348 removal from a site.

The threshold sensor scheme shown in the examples of FIGS. 7-and 8 can be broadened to use more than one sensor 60. Referring to the block diagram of FIG. 9, there is shown a network 76 of sensors 60a, 60b, 60c, and 60d for tracking movement of mobile DR imaging apparatus 310 within a hospital or other facility. Network 76 can be wired or wireless, or have both wired and wireless connections to processor 36. A record of DR detector 348 travel can be maintained so that the last location of this device can be quickly determined. A logic scheme can be set up that permits transit past sensors in certain areas, optionally recording the transit event but taking no other action, but signals an alarm for transit past other sensors. Thus, in the simplified example of FIG. 9, transit of detector 348 past sensors 60a, 60b, and 60c is recorded by processor 36, but no warning indication is provided. However, transit past sensor 60d indicates unauthorized removal from a designated area and triggers an alarm indication. Various alarms, indicators, or status messages on console 40 can then help to alert personnel to the location of and proper use of the detector within the facility. With a similar function, the block diagram of FIG. 10 uses a GPS system or other wireless geographic locator as part of tracking system 100 to identify the location of mobile DR imaging apparatus 310 and its associated detector 348 and provide a signal indicative of detector location. Cellular network tracking may alternately be used for this purpose. According to an alternate embodiment of the present invention, proximity to a Wireless Access Point, such as provided within the hospital or other facility or provided with the DR system itself.

According to an alternate embodiment of the present invention, DR detector 348 periodically provides a signal indicative of its location within a hospital or other site in a "phone-home" manner, using a wireless network that is associated with the site. A cell phone device associated with the detector 348 dials in its location every few minutes, enabling accurate tracking. Battery backup can be provided so that this feature operates even when a battery is low or is removed from its intended position. Alternately, a website, indexed using the unique identifier of the detector 348, may be continually updated with this information to provide location data for the detector, a signal indicative of its location.

Figure 11A:
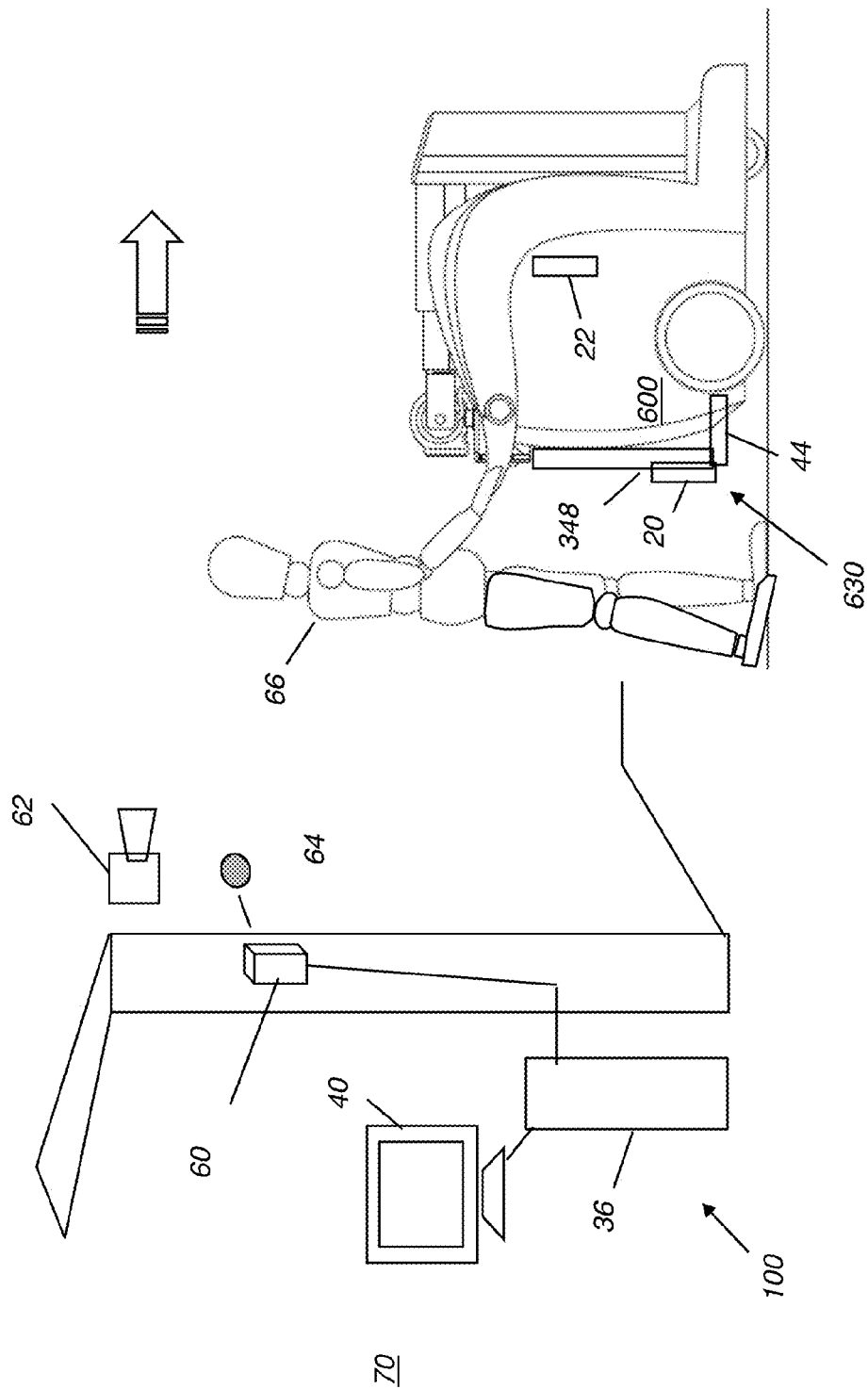
FIG. 11A is a schematic diagram showing a mobile radiography apparatus moving past a sensor with the DR detector properly registered to the x-ray system.
Figure 11B:
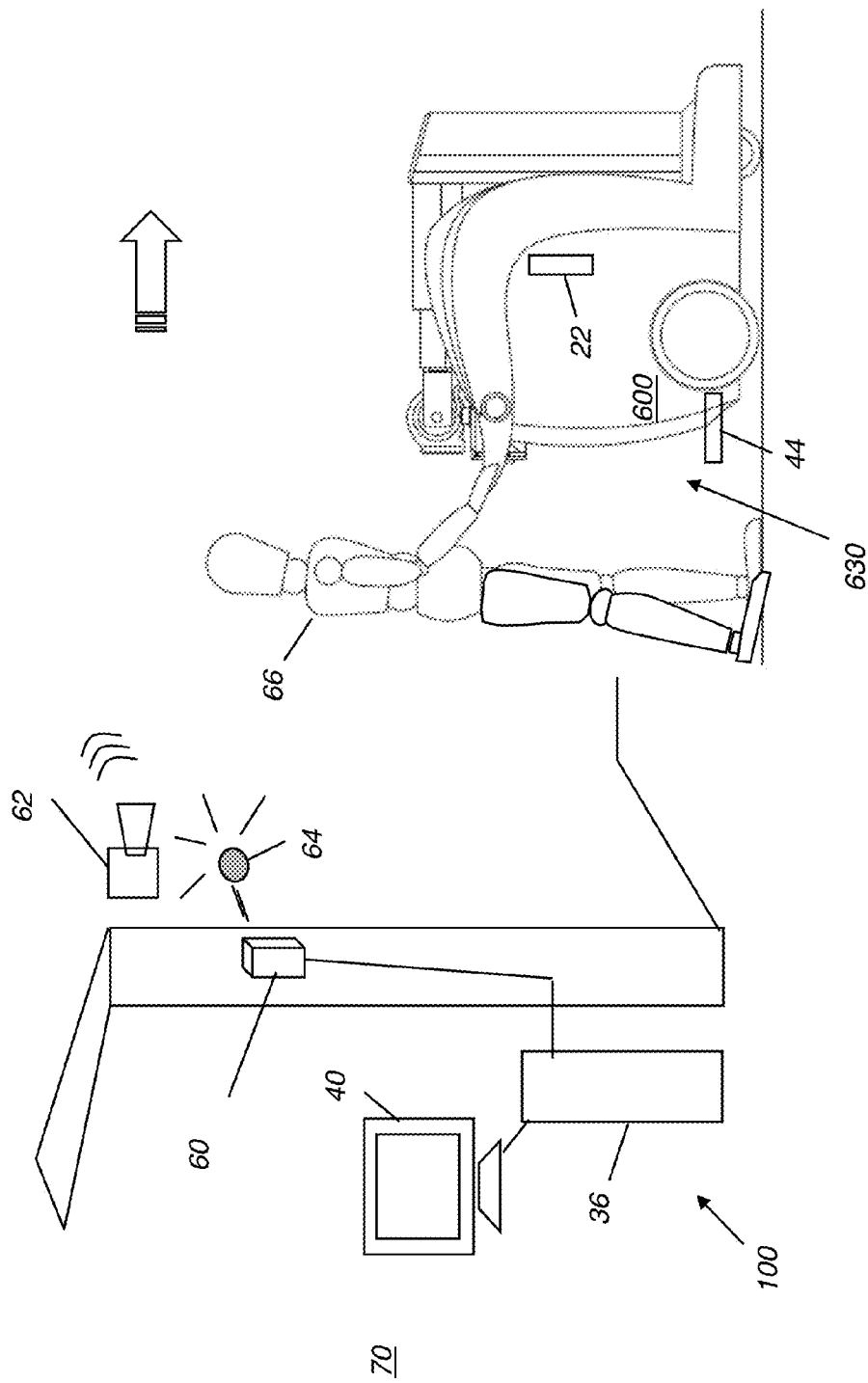
FIG. 11B is a schematic diagram showing a mobile radiography apparatus moving past a sensor in an error state.

FIGS. 11A and 11B show movement of mobile radiography apparatus 600 past sensor 60 in an alternate tracking embodiment of the present invention. An identifier 22 on radiography apparatus 600 is also sensed by sensor 60, helping to uniquely identify and track the relative position of mobile radiography apparatus 600 as well as that of DR detector 348. When DR detector 348 is properly registered to, and seated in transport position within, mobile radiography apparatus 600, as shown in FIG. 11A, sensor 60 detects this condition and no warning or alarm is provided. Thus, when DR detector 348 and mobile apparatus 600 are properly associated with each other, normal behavior can be assumed when both pass sensor 60 and no tracking discrepancy is suspected. If, however, only radiography apparatus 600 or, alternately, only DR detector 348 is detected crossing a threshold, the sensor 60 signal is used by tracking system 100 to indicate a tracking discrepancy and to provide a suitable alarm or warning indication. FIG. 11B shows technician 66 moving radiography system 600, without its associated DR detector 348, past sensor 60, causing a warning to be issued.

Figure 12:
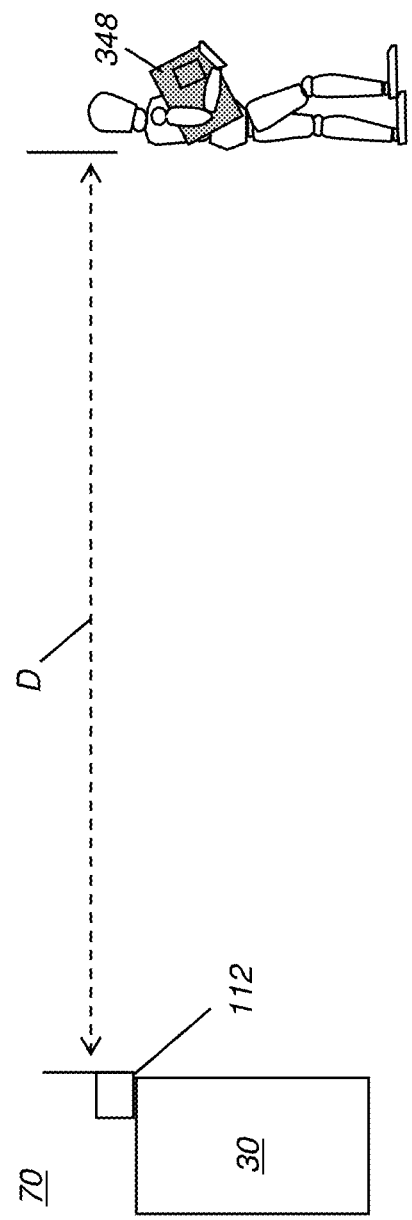
FIG. 12 is a schematic diagram showing distance detection from a stationary x-ray system.
Figure 13:
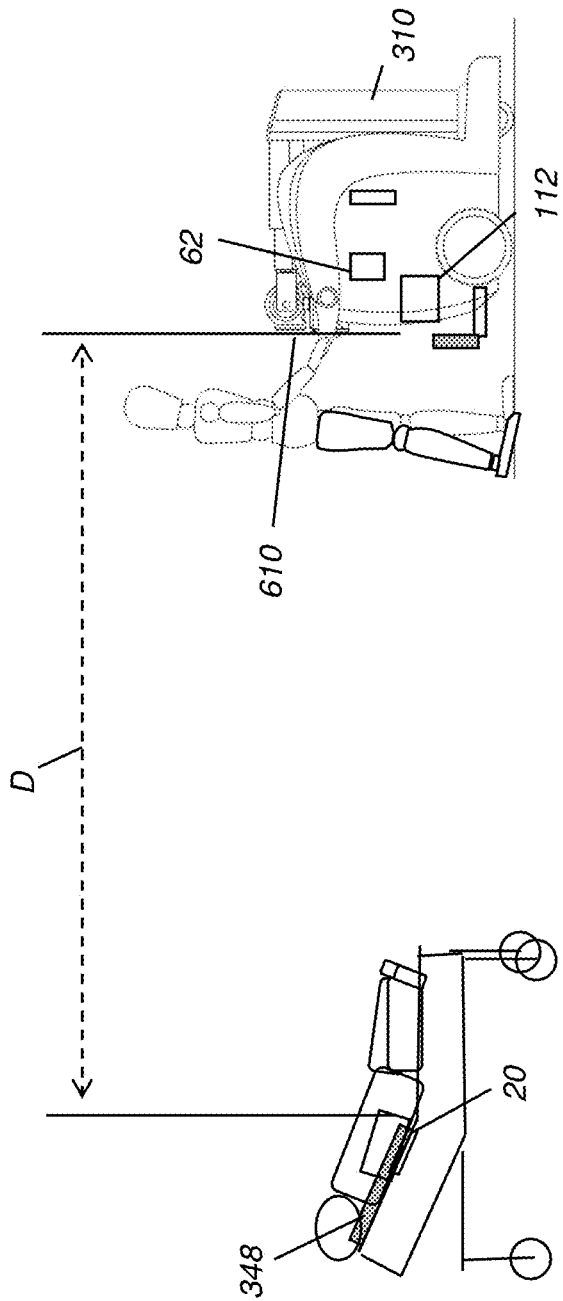
FIG. 13 is a schematic diagram showing distance detection from a portable x-ray system.

FIGS. 12 and 13 show an alternative to crossing a threshold that can be used by tracking system 100 for tracking the location of DR detector 348 relative to stationary x-ray site 70 or mobile radiography apparatus 310, respectively. Referring back to the model of FIG. 4, a distance sensor 112 is used as part of tracking system 100. When DR detector 348 exceeds distance D from sensor 112, tracking system 100 detects a discrepancy in detector 348 location and generates a warning signal. Distance D is predetermined, and is programmable for a particular site according to an embodiment of the present invention. In the mobile apparatus embodiment of FIG. 13, for example, a programmed value of 20 feet is used for distance D. When the distance between DR detector 348 and distance sensor 112 exceeds this value, alarm 62 beeps a number of times and a message appears for the technician on the operator console, display 610.

Figure 14:
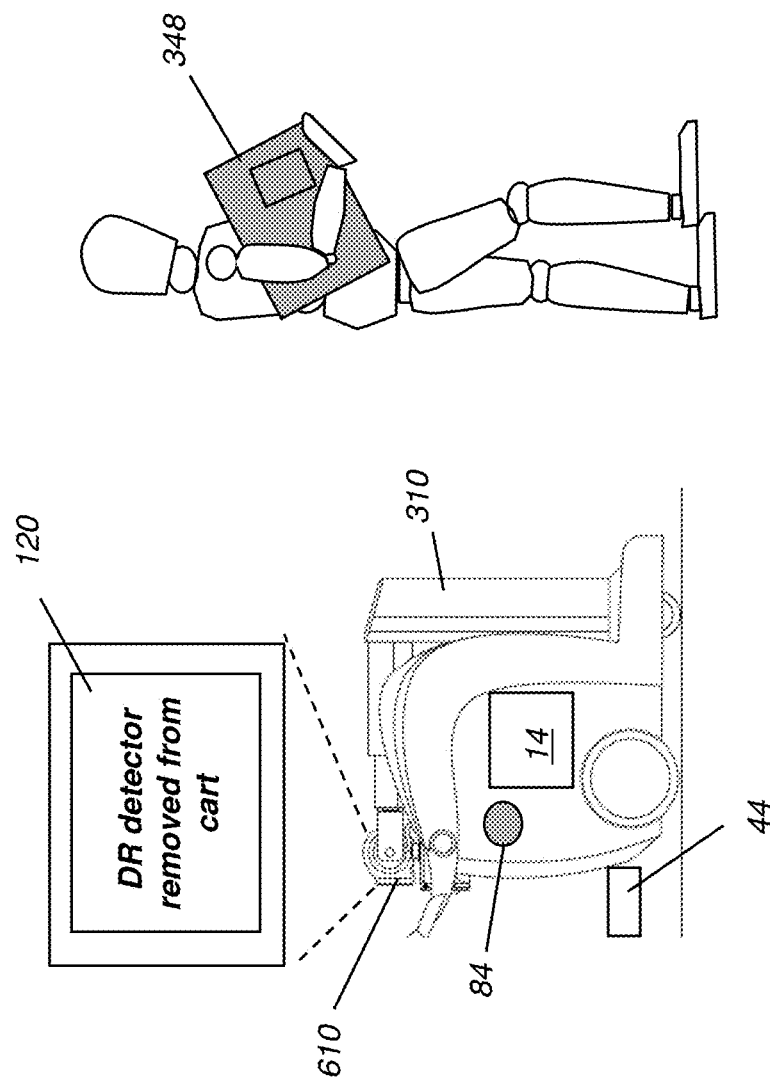
FIG. 14 is a schematic diagram showing a reminder message displayed at a portable x-ray system.

The schematic block diagram of FIG. 14 shows an alternate embodiment of the present invention, in which removal of DR detector 348 from near proximity to sensor 44 on apparatus 310 causes a message 120 to be displayed on display 610. Alternately, a flashing on-screen symbol or screen message is provided whenever detector 348 is removed for any reason, or is out of range for a length of time that exceeds a preset timeout interval. For example, it can be allowable for DR detector 348 to be removed from its seated position adjacent sensor 44 for up to 6 minutes, or other timeout interval that is determined to allow sufficient time for obtaining an image using the system. Thus, the operator is informed of possible detector loss or misplacement only after a period of time elapses, indicating failure to return the detector to its storage position or an unexpected pattern of use. An optional alarm 14 or indicator 84 may also be provided to indicate removal of DR detector 348 for a time exceeding a threshold. A supervisor override switch or command can also be provided on x-ray system 30, allowing supervisory personnel to remove a particular detector 348 from a site without causing an alarm indication.

Inconsistent or unexpected events or behavior can also cause an alarm indication. Thus, for example, an alert can be issued when the cart or transport frame of the mobile imaging apparatus is in motion for a period of time, such as for more than 10 seconds, without a detector 348. As with other methods noted earlier, an excessive distance between the cart and corresponding detector can trigger an alarm condition. This alarm condition can be reported by a signal that is generated at any number of locations, including at a remote location, at the operator console, within the processor, on the cart itself, on the DR detector itself, or at multiple locations, for example. The signal that is generated can be a voltage level or analog signal, a digital signal, or an encoded digital data element, such as a byte of data or a command that is generated within the processor or other digital logic circuit, for example.

Figure 15:
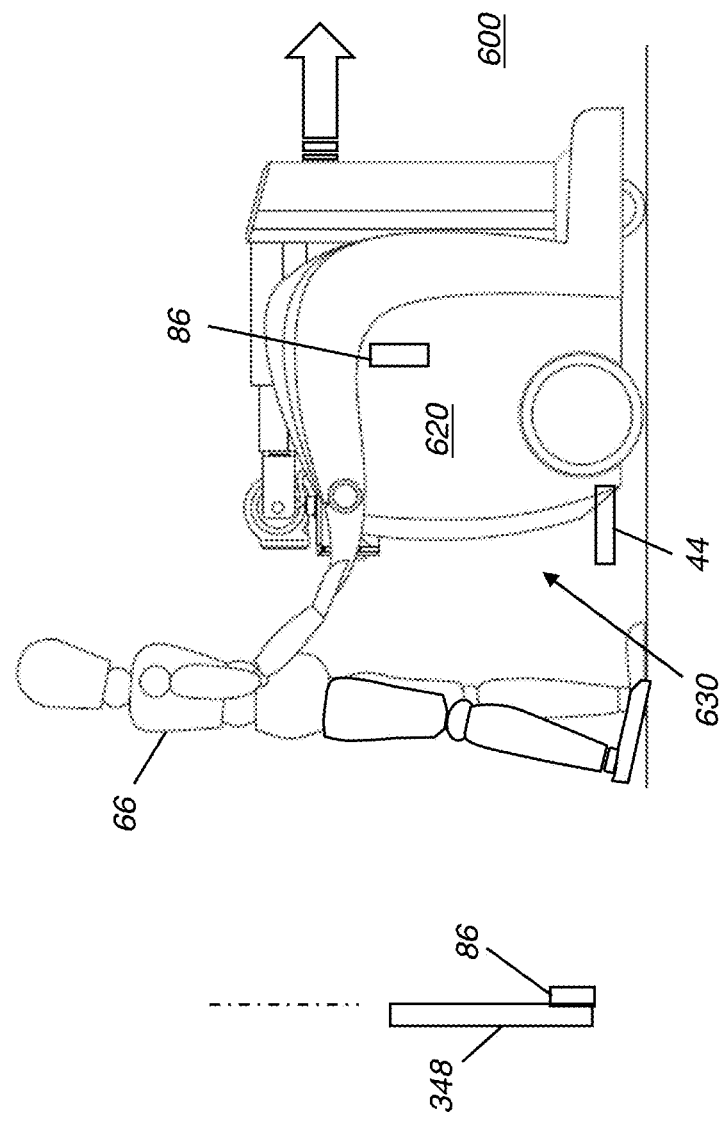
FIG. 15 is a schematic diagram showing motion detection used to sense a missing detector for a portable x-ray system.

Consistent with an alternate embodiment of the present invention, relative movement of either DR detector 348 or its associated mobile apparatus 600 is sensed as a tracking indicator. The schematic block diagram of FIG. 15 shows a motion sensor 86 at each of detector 348 and transport frame 620. After allowing for a standard motion pattern needed for imaging, such as would be necessary to adjust the position of the detector 348, transport frame 620, or both, motion sensors 86 can be used to provide information that indicates transport of either the detector or the portable frame away from each other. The technician 66 can be informed by an alarm or by a message indicating that detector 348 is separated or is moving apart from the portable radiography system.

Various types of sensors can be used in embodiments of the present invention, to detect movement passed a point or across a threshold, as sensor 60 in FIGS. 7-11B; movement beyond a predetermined distance D, as sensor 112 in FIGS. 12 and 13, or as motion sensors 86 as shown in FIG. 15. According to an embodiment of the present invention, sensor 60, for example, is a radio-frequency (RF) transceiver that communicates with an RFID tag or similar RF transponder device that comes within a given distance. Advantageously, the RF transponder can be of the passive type, so that it obtains power from the transceiver signal, eliminating the need to provide battery or other support power for identifier 20 on the DR detector. Alternately, an on-board battery can be provided for the RF transponder. RFID technology is widely used for assets tracking and loss management, such as in retail environment, and has also been used in the hospital environment, such as for tracking infants, for example.

In an alternate embodiment, one or more wireless routers at the site provide the function of sensor 60. Wireless access protocols are generated to activate communication between the DR detector 348 and the wireless router that acts as sensor 60. Loss of communication due to poor signal strength can be used to signal movement past a threshold location.

Thus, in FIG. 7, for example, identifier 20 is an RFID tag that has a unique encoded identifier for DR detector 348. This configuration is advantaged for relatively low cost and ease of use. Other wireless solutions may be more costly and complex than the RFID approach, but may afford other advantages and may be more robust. Alternate solutions can include the use of ZigBee based on IEEE 802, Bluetooth, IEEE 812.11a/b/g/n, and other short range wireless devices.

Where distance is used to determine a tracking discrepancy, as shown in embodiments of FIGS. 12 and 13, signal strength can be used to determine when a predetermined distance D between detector 348 and system 30 (such as a stationary x-ray system or mobile imaging apparatus 310) exceeds a given value. Where signal strength drops below a certain predetermined level, or drops out altogether, distance D has been exceeded. Short range wireless transmission protocols, such as Bluetooth and ZigBee, for example, have this advantage, by which transmission quality and detectability drops quickly beyond a given, limited distance.

Sensor 44 on transport frame 620, as shown in FIGS. 11A, 11B, and 14, can be a proximity sensor that senses the presence of DR detector 348, in its transport position in storage area 630 or may be a toggle switch, optical switch, or other switch that is actuated when the detector 348 is properly seated in or removed from its storage area 630 on transport frame 620. According to an alternate embodiment of the present invention, sensor 44 is an RFID transceiver or similar device.

In an alternate embodiment, tracking system 100 records use and detection events for each mobile radiography apparatus 600, which provides a log of information that shows where DR detector 348 was last used. Where threshold sensors 60 are provided, tracking system 100 also records the location of the sensor 60 that last detected a particular DR detector 348 and records the time. This time-stamped information is accessed for display from console 40 or, alternately, from display 610 on apparatus 600. Tracking information may also be provided from a Hospital Information System (HIS) or Radiography Information System (RIS) or as data stored in DICOM format for the patient.

Only a small amount of control logic is needed from processor 36 to determine whether or not an alarm or warning should be issued. Registration helps to organize tracking operation and signal processing and, because it correlates DR detectors to imaging systems, helps to prevent false positive alarms that can annoy hospital personnel and frustrate the purposes of the tracking system.

According to an embodiment of the present invention, DR detector 348 has a communication channel that is disabled unless detector 348 is within a prescribed distance of its associated x-ray system 30.

It can be appreciated that embodiments of the present invention help to reduce false-positive indications of possible theft or misrouting of the DR detector. By registering each DR detector 348 to one or more x-ray systems (stationary or portable), embodiments of the present invention help to eliminate sending alarms when unnecessary, such as when a new DR detector is in transit between hospital departments, for example.

According to an alternate embodiment, detector 348 is locked in its transport position in storage area 630 of mobile DR imaging apparatus 310 when left unattended. An in-room system or portable system storage can lock the detector 348 until a valid user logs into the system or properly logs out the detector. Users can have a method of unregistering a DR detector 348 from a console so that it does not activate the alarm when passing through a doorway or moving out of range. This is done at the Console PC (e.g., facility, in-room or mobile system) that is in communication with the sensors at the doorway or with the wireless detection system. If the technician forgets to unregister the detector from a system and sets off the alarm, the technician or other appropriate personnel can deactivate the alarm at the doorway.

Exemplary deactivation of an alarm or indicator can include pressing a button, entering a code at a keypad, swiping/scanning a badge at a card reader, or other action. Deactivating the alarm could automatically unregister the detector from the system it is currently associated with or display a prompt at the console asking if the operator wants to unregister the detector.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

In one embodiment, the second display 610' and/or the first display 610 can be actuated for example using an attached keyboard/mouse, a remote control, a touch screen, a tethered control, an operable screen or the like. In one embodiment, the first display 610 can implement a subset of the functionality of the second display 610'. In another embodiment, the second display 610' can implement a subset of the functionality of the first display 610. Alternatively, information and controls capable of use at the first display 610 can be provided (e.g., identically) at the second display 610'.

As will be appreciated by one skilled in the art, the present invention may be embodied as a system or method, with parts of the system executed using a computer program product. Accordingly, an embodiment of the present invention may be in the form of an entirely hardware embodiment or an embodiment combining software and hardware aspects that may all generally be referred to herein as a "circuit" or "system." Furthermore, parts of the present invention may take the form of a computer program product embodied in a computer-readable storage medium, with instructions executed by one or more computers or host processors. This medium may comprise, for example: magnetic storage media such as a magnetic disk (such as a hard drive or storage disk) or magnetic tape; optical storage media such as an optical disc, optical tape, or machine readable bar code; solid state electronic storage devices such as solid state hard drives, random access memory (RAM), or read only memory (ROM); or any other physical device or medium employed to store a computer program. The computer program for performing the method of the present invention may also be stored on computer readable storage medium that is connected to a host processor by way of the internet or other communication medium.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

Those skilled in the art will readily recognize that the equivalent of such a computer program product may also be constructed in hardware. The computer-usable or computer-readable medium could even be paper or another suitable medium upon which executable instructions are printed, as the instructions can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport computer instructions for use by, or in connection with, an instruction execution system, apparatus, or device.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for managing a portable x-ray detector for an x-ray imaging apparatus, the method comprising:
    registering at least one portable detector with a processor that is associated with the x-ray imaging apparatus;
    generating a signal that is indicative of the location of the registered portable x-ray detector relative to the x-ray imaging apparatus; and
    providing an alert indication when the generated signal indicates separation of the registered portable x-ray detector from the x-ray imaging apparatus beyond a predetermined distance.

2. The method of claim 1 where the alert indication is an audible or visual indication.

3. The method of claim 1 wherein the distance is greater than 20 feet.

4. The method of claim 1 wherein the alert indication is provided by the registered portable x-ray detector or by an operator console.

5. The method of claim 1 where the alert indication is a message that displays at an operator console associated with the x-ray imaging apparatus.

6. The method of claim 1 wherein the x-ray imaging apparatus is a portable x-ray imaging apparatus.

7. The method of claim 6, where the alert indication is configured to occur as the portable x-ray imaging apparatus moves away from the at least one portable detector or where the alert indication is configured to occur as the at least one portable detector moves away from the portable x-ray imaging apparatus.

8. A portable x-ray imaging apparatus comprising:
    a moveable transport frame;
    an adjustable support structure coupled to the movable transport frame;
    an x-ray source mounted to the adjustable support structure;
    at least one portable radiographic detector registered at the portable x-ray imaging apparatus and having an identifier that is coupled to the portable detector; and
    an alert indicator at the portable x-ray imaging apparatus, where the alert indicator is configured to operate when the at least one registered portable radiographic detector is greater than a prescribed distance from the mobile x-ray imaging apparatus.

9. The apparatus of claim 8 wherein the alert indicator operates when a wireless communications signal strength drops below a prescribed threshold or when wireless communications from the portable x-ray imaging apparatus to the at least one registered portable radiographic detector is interrupted.

10. The apparatus of claim 8 wherein the alert indicator provides an audible or visual indication.

11. The apparatus of claim 8 wherein the alert indicator operates when the prescribed distance exceeds 20 feet.

12. The apparatus of claim 8 wherein the alert indicator is configured to also occur at the at least one registered portable radiographic detector.

13. An x-ray radiography apparatus comprising:
an x-ray imaging area enclosing at least one x-ray imaging system including an x-ray source;
at least one sensor positioned at an entrance to the x-ray imaging area;
at least one portable radiographic detector registered to the x-ray imaging area; and
an alert indication at the entrance to the x-ray imaging area or at the at least one portable radiographic detector or at an operator console, where the alert indication is configured to operate when the at least one registered portable radiographic detector accesses the entrance to the x-ray imaging area.

14. The apparatus of claim 13 wherein the alert indication is an audible or visual indication.

15. The apparatus of claim 13 wherein an unregistered detector does not trigger the alert.

16. The apparatus of claim 13, wherein the operator console includes a processor to control operations at the x-ray apparatus and wherein the at least one registered portable radiographic detector is registered at the console.

17. The apparatus of claim 16 wherein the console provides an operator interface that allows an operator to register or to un-register the at least one registered portable radiographic detector.

18. The apparatus of claim 13 wherein the alert indication is not actuated when an authorized person accompanies the at least one portable radiographic detector in accessing the entrance to the x-ray imaging area.

19. A mobile x-ray imaging apparatus comprising:
a moveable transport frame;
an adjustable support structure coupled to the movable transport frame;
an x-ray source mounted to the adjustable support structure;
a sensor that provides a signal that is indicative of the presence or absence of a portable radiographic detector in a transport position on the mobile x-ray imaging apparatus; and
an alert indicator that is configured to operate when the portable radiographic detector is not in the transport position, according to the sensor signal.

20. The apparatus of claim 19, wherein the portable detector is registered at the mobile x-ray imaging apparatus, the portable detector includes an identifier that is coupled thereto, and wherein the apparatus further comprises an alert indicator that is activated when a wireless communication signal strength between the portable detector and the mobile x-ray imaging apparatus drops below a preselected threshold.

* * * * *